(12) United States Patent
Sidhu et al.

(10) Patent No.: US 12,661,285 B2
(45) Date of Patent: Jun. 23, 2026

(54) TECHNIQUES FOR MANAGING PATIENT THERAPY PROTOCOLS

(71) Applicant: Stryker Corporation, Portage, MI (US)

(72) Inventors: Anuj Sidhu, Kalamazoo, MI (US);
Alexander Bodurka, Portage, MI (US);
Krishna Sandeep Bhimavarapu,
Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 19/024,194

(22) Filed: Jan. 16, 2025

(65) Prior Publication Data

US 2025/0152440 A1 May 15, 2025

Related U.S. Application Data

(63) Continuation of application No. 18/543,378, filed on Dec. 18, 2023, now Pat. No. 12,239,591, which is a
(Continued)

(51) Int. Cl.
*A61G 7/018* (2006.01)
*A61G 7/00* (2006.01)
(Continued)

(52) U.S. Cl.
CPC ............. *A61G 7/018* (2013.01); *A61G 13/02* (2013.01); *G16H 10/60* (2018.01); *G16H 20/30* (2018.01);
(Continued)

(58) Field of Classification Search
CPC ...... A61G 7/018; A61G 13/02; A61G 7/1046; A61G 7/0506; A61G 7/0524; A61G 7/001;
(Continued)

(56) References Cited

U.S. PATENT DOCUMENTS 6,804,656 B1 10/2004 Rosenfeld et al.
7,109,848 B2 9/2006 Schybergson
(Continued)

FOREIGN PATENT DOCUMENTS

CA 2378005 C 11/2005
EP 2040188 A1 3/2009
(Continued)

*Primary Examiner* — Robert G Santos
(74) *Attorney, Agent, or Firm* — Howard & Howard Attorneys PLLC

(57) ABSTRACT

A system and a method for managing patient therapy protocols are disclosed. The system includes a patient support apparatus for supporting a patient, a first input device for use by a first caregiver, a location system for determining a location of the first caregiver, and a therapy management system. The therapy management system receives a location of the first caregiver and a selection of a patient therapy protocol, which includes a location requirement. The therapy management system then determines whether the first caregiver location input signal satisfies the location requirement before initiating the selected patient therapy protocol or notifying a second caregiver if the location of the first caregiver does not satisfy the location requirement.

20 Claims, 8 Drawing Sheets

Related U.S. Application Data continuation of application No. 18/127,896, filed on Mar. 29, 2023, now Pat. No. 11,890,241, which is a continuation of application No. 17/409,988, filed on Aug. 24, 2021, now Pat. No. 11,642,261, which is a continuation of application No. 16/211,927, filed on Dec. 6, 2018, now Pat. No. 11,123,246.

(60) Provisional application No. 62/609,805, filed on Dec. 22, 2017.

(51) Int. Cl.

| | |
|---|---|
| *A61G 7/05* | (2006.01) |
| *A61G 7/10* | (2006.01) |
| *A61G 13/02* | (2006.01) |
| *G16H 10/60* | (2018.01) |
| *G16H 20/30* | (2018.01) |
| *G16H 40/20* | (2018.01) |
| *G16H 40/63* | (2018.01) |

(52) U.S. Cl.
CPC ............. *G16H 40/20* (2018.01); *G16H 40/63* (2018.01); *A61G 7/001* (2013.01); *A61G 7/0506* (2013.01); *A61G 7/0524* (2016.11); *A61G 7/1046* (2013.01)

(58) Field of Classification Search
CPC ........ G16H 10/60; G16H 20/30; G16H 40/20; G16H 40/63
USPC ............................................ 5/613, 616, 600
See application file for complete search history.

(56) References Cited

U.S. PATENT DOCUMENTS

| | | | |
|---|---|---|---|
| 7,307,543 | B2 | 12/2007 | Rosenfeld et al. |
| 7,319,386 | B2 | 1/2008 | Collins, Jr. et al. |
| 7,321,862 | B2 | 1/2008 | Rosenfeld et al. |
| 7,433,827 | B2 | 10/2008 | Rosenfeld et al. |
| 7,454,359 | B2 | 11/2008 | Rosenfeld et al. |
| 7,467,094 | B2 | 12/2008 | Rosenfeld et al. |
| 7,557,689 | B2 | 7/2009 | Seddigh et al. |
| 7,650,291 | B2 | 1/2010 | Rosenfeld et al. |
| 7,808,391 | B2 | 10/2010 | Nixon |
| 7,958,201 | B2 | 6/2011 | Lindsay |
| 8,170,887 | B2 | 5/2012 | Rosenfeld et al. |
| 8,175,895 | B2 | 5/2012 | Rosenfeld et al. |
| 8,856,383 | B2 | 10/2014 | Beninato et al. |
| 9,094,723 | B2 | 7/2015 | Reams |
| 9,185,202 | B2 | 11/2015 | Herbst et al. |
| 9,204,823 | B2 | 12/2015 | Derenne et al. |
| 9,305,450 | B2 | 4/2016 | Halverson et al. |
| 9,307,033 | B1 | 4/2016 | Meschkat |
| 9,513,899 | B2 | 12/2016 | Collins, Jr. et al. |
| 9,584,965 | B2 | 2/2017 | Good et al. |
| 9,737,454 | B2 | 8/2017 | Hornbach et al. |
| 9,833,194 | B2 | 12/2017 | Hayes et al. |

| | | | | |
|---|---|---|---|---|
| 10,068,116 | B2 | 9/2018 | Good et al. | |
| 10,542,382 | B2 | 1/2020 | Good et al. | |
| 10,679,748 | B2 | 6/2020 | Durlach et al. | |
| 10,905,611 | B2 | 2/2021 | Sidhu et al. | |
| 10,943,678 | B2 | 3/2021 | Hornbach et al. | |
| 11,011,272 | B2 | 5/2021 | Durlach et al. | |
| 11,123,246 | B2 | 9/2021 | Sidhu et al. | |
| 11,468,986 | B2 | 10/2022 | Durlach et al. | |
| 11,642,261 | B2 | 5/2023 | Sidhu et al. | |
| 11,769,590 | B2 | 9/2023 | Durlach et al. | |
| 11,890,241 | B2 | 2/2024 | Sidhu et al. | |
| 12,239,591 | B2 * | 3/2025 | Sidhu | G16H 40/63 |
| 12,285,373 | B2 * | 4/2025 | Sidhu | A61G 7/0524 |
| 2002/0014951 | A1 | 2/2002 | Kramer et al. | |
| 2005/0159987 | A1 | 7/2005 | Rosenfeld et al. | |
| 2005/0177400 | A1 | 8/2005 | Rosenfeld et al. | |
| 2005/0187796 | A1 | 8/2005 | Rosenfeld et al. | |
| 2005/0203777 | A1 | 9/2005 | Rosenfeld et al. | |
| 2006/0022834 | A1 | 2/2006 | Rosenfeld et al. | |
| 2006/0025657 | A1 | 2/2006 | Rosenfeld et al. | |
| 2006/0064324 | A1 | 3/2006 | Rosenfeld et al. | |
| 2006/0085227 | A1 | 4/2006 | Rosenfeld et al. | |
| 2006/0085229 | A9 | 4/2006 | Rosenfeld et al. | |
| 2006/0122869 | A9 | 6/2006 | Rosenfeld et al. | |
| 2006/0161459 | A9 | 7/2006 | Rosenfeld et al. | |
| 2007/0174964 | A1 | 8/2007 | Lemire et al. | |
| 2011/0307284 | A1 | 12/2011 | Thompson et al. | |
| 2012/0284053 | A1 | 11/2012 | Rosenfeld et al. | |
| 2013/0231596 | A1 | 9/2013 | Hornbach et al. | |
| 2014/0031730 | A1 | 1/2014 | Hornbach et al. | |
| 2014/0046674 | A1 | 2/2014 | Rosenfeld et al. | |
| 2014/0259414 | A1 | 9/2014 | Hayes et al. | |
| 2014/0297327 | A1 | 10/2014 | Heil et al. | |
| 2015/0281659 | A1 | 10/2015 | Hood et al. | |
| 2016/0026837 | A1 | 1/2016 | Good et al. | |
| 2016/0199240 | A1 | 7/2016 | Newkirk et al. | |
| 2016/0259906 | A1 | 9/2016 | Iucha et al. | |
| 2016/0367420 | A1 | 12/2016 | Zerhusen et al. | |
| 2017/0124366 | A1 | 5/2017 | Good et al. | |
| 2017/0333279 | A1 | 11/2017 | Hornbach et al. | |
| 2019/0082298 | A1 | 3/2019 | Good et al. | |
| 2019/0192366 | A1 | 6/2019 | Sidhu et al. | |
| 2019/0192368 | A1 | 6/2019 | Sidhu et al. | |
| 2019/0198167 | A1 | 6/2019 | Durlach et al. | |
| 2019/0198168 | A1 | 6/2019 | Lee et al. | |
| 2020/0258626 | A1 | 8/2020 | Durlach et al. | |
| 2021/0106478 | A1 | 4/2021 | Sidhu et al. | |
| 2021/0241904 | A1 | 8/2021 | Durlach et al. | |
| 2021/0393460 | A1 | 12/2021 | Sidhu et al. | |
| 2022/0415501 | A1 | 12/2022 | Durlach et al. | |
| 2023/0233390 | A1 | 7/2023 | Sidhu et al. | |
| 2024/0115443 | A1 | 4/2024 | Sidhu et al. | |
| 2025/0152440 | A1 * | 5/2025 | Sidhu | G16H 40/63 |
| 2025/0228722 | A1 * | 7/2025 | Sidhu | A61G 7/0524 |

FOREIGN PATENT DOCUMENTS

| | | | |
|---|---|---|---|
| EP | 1200924 B1 | 4/2014 | |
| WO | 0079466 A2 | 12/2000 | |
| WO | 2011156597 A1 | 12/2011 | |

* cited by examiner

TECHNIQUES FOR MANAGING PATIENT THERAPY PROTOCOLS

CROSS-REFERENCE TO RELATED APPLICATIONS

The subject patent application is a Continuation of U.S. patent application Ser. No. 18/543,378 filed on Dec. 18, 2023 and issued as U.S. Pat. No. 12,239,591 on Mar. 4, 2025, which is a Continuation of U.S. patent application Ser. No. 18/127,896 filed on Mar. 29, 2023 and issued as U.S. Pat. No. 11,890,241 on Feb. 6, 2024, which is a Continuation of U.S. patent application Ser. No. 17/409,988 filed on Aug. 24, 2021 and issued as U.S. Pat. No. 11,642,261 on May 9, 2023, which is a Continuation of U.S. patent application Ser. No. 16/211,927 filed on Dec. 6, 2018 and issued as U.S. Pat. No. 11,123,246 on Sep. 21, 2021, which claims priority to and all the benefits of U.S. Provisional Patent Application No. 62/609,805 filed on Dec. 22, 2017, the disclosures of each of which are hereby incorporated by reference in their entirety.

BACKGROUND

Patient therapy protocols may be used to periodically provide therapy to a patient via a medical device. Such medical devices may include, for example, patient support apparatuses, such as hospital beds, stretchers, cots, tables, wheelchairs, recliners, and chairs for patient care. Other medical devices may include equipment such as lights, televisions, temperature management systems, respirators, IV lines, surgical tools, and heart rate monitors that may be used in medical procedures or in the provision of medical services to patients. For example, a patient therapy protocol may be used to periodically provide therapy to a patient disposed on a patient support apparatus by turning the patient every hour to minimize the patient's risk for developing a pressure ulcer.

Typically, patient therapy protocols may be initiated by a caregiver assigned to the patient or the patient support apparatus. However, such caregivers are typically tasked with caring for multiple patients. Furthermore, because patient therapy protocols may periodically provide therapy to the patient after being initiated, there is a possibility that the caregiver may forget that the patient therapy protocol is providing therapy to the patient. As such, there are opportunities to address at least the aforementioned problems.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Referring to the Figures, wherein like numerals indicate like or corresponding parts throughout the several views, techniques for managing patient therapy protocols are provided.

Figure 1:
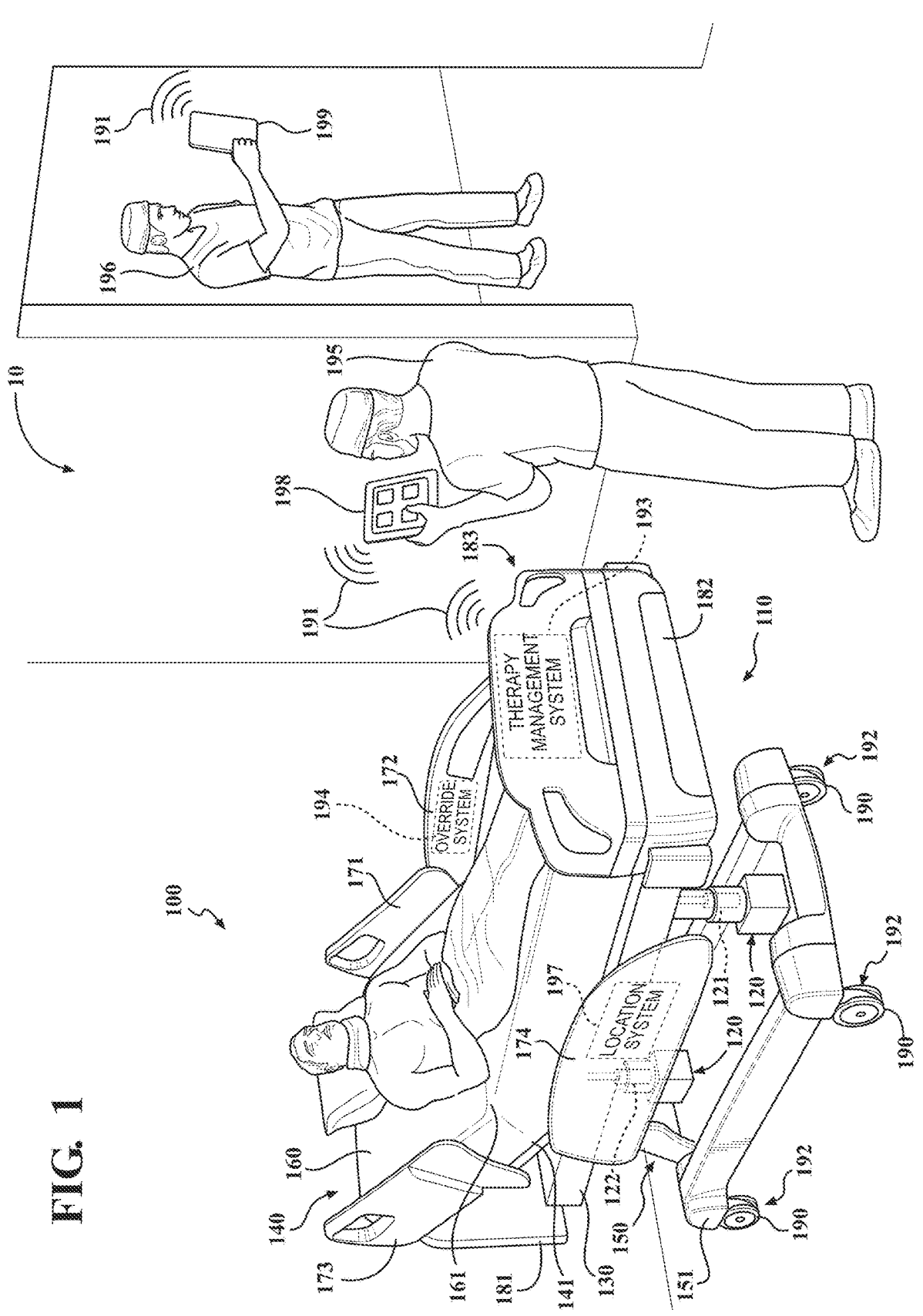
FIG. 1 is a perspective view of a system including a patient support apparatus, input devices, a location system, and a therapy management system.

Referring to FIG. 1, an embodiment of a system 10 for managing patient therapy protocols is shown. The system 10 includes a patient support apparatus 100 for supporting a patient in a health care setting. The patient support apparatus 100 illustrated in FIG. 1 includes a hospital bed. However, in other embodiments, the patient support apparatus 100 may include a stretcher, a cot, a table, a wheelchair, a recliner, a chair for patient care, or any other similar apparatus utilized in the care of a patient.

A support structure 110 provides support for the patient. The support structure 110 illustrated in FIG. 1 includes a base 150 and a support frame 130. The base 150 includes a base frame 151. The support frame 130 is spaced above the base frame 151 in FIG. 1. The support structure 110 also includes a patient support deck 140 disposed on the support frame 130. The patient support deck 140 includes several sections, some of which are capable of articulating relative to the support frame 130, such as a back section, a seat section, a thigh section, and a foot section. The patient support deck 140 provides a patient support surface 141 upon which the patient is supported.

A mattress 160 may be disposed on the patient support deck 140 during use. The mattress 160 includes a secondary patient support surface 161 upon which the patient is supported. In addition, the mattress 160 may be omitted in certain embodiments, such that the patient rests directly on the patient support surface 141.

The base 150, support frame 130, patient support deck 140, and patient support surface 141 each have a head end and a foot end corresponding to a designated placement of the patient's head and feet on the patient support apparatus 100. The construction of the support structure 110 may take on any suitable design, and is not limited to that specifically set forth above.

Side rails 171, 172, 173, 174 are coupled to the support frame 130 or the patient support deck 140 and are thereby supported by the base 150. A first side rail 171 is positioned at a left head end of the patient support deck 140. A second side rail 172 is positioned at a left foot end of the support frame 130. A third side rail 173 is positioned at a right head end of the patient support deck 140. A fourth side rail 174 is positioned at a left foot end of the support frame 130. If the patient support apparatus 100 is a stretcher or a cot, there may be fewer side rails. The side rails 171, 172, 173, 174 are movable to a raised position in which they block ingress and egress into and out of the patient support apparatus 100, one or more intermediate positions, and a lowered position in which the side rails 171, 172, 173, 174 are not an obstacle to such ingress and egress. In still other configurations, the patient support apparatus 100 may not include any side rails.

A headboard 181 and a footboard 182 are coupled to the support frame 130. In other embodiments, when the headboard 181 and footboard 182 are included, the headboard 181 and footboard 182 may be coupled to other locations on the patient support apparatus 100, such as the base 150. In still other embodiments, the patient support apparatus 100 does not include the headboard 181 and/or the footboard 182.

Caregiver interfaces 183, such as handles, are shown integrated into the footboard 182 and side rails 171, 172, 173, 174 to facilitate movement of the patient support apparatus 100 over floor surfaces. Additional caregiver interfaces 183 may be integrated into the headboard 181 and/or other components of the patient support apparatus 100. The caregiver interfaces 183 are graspable by a caregiver to manipulate the patient support apparatus 100 for movement.

Wheels 190 are coupled to the base 150 to facilitate transport over the floor surfaces. The wheels 190 are arranged in each of four quadrants of the base 150 adjacent to corners of the base 150. In the embodiment shown, the wheels 190 are caster wheels able to rotate and swivel relative to the support structure 110 during transport. Each of the wheels 190 forms part of a caster assembly 192. Each caster assembly 192 is mounted to the base 150. It should be understood that various configurations of the caster assemblies 192 are contemplated. In addition, in some embodiments, the wheels 190 are not caster wheels and may be non-steerable, steerable, non-powered, powered, or combinations thereof. Additional wheels are also contemplated. For example, the patient support apparatus 100 may include four non-powered, non-steerable wheels, along with one or more powered wheels. In some cases, the patient support apparatus 100 may not include any wheels.

In other embodiments, one or more auxiliary wheels (powered or non-powered), which are movable between stowed positions and deployed positions, may be coupled to the support structure 110. In some cases, when these auxiliary wheels are located between caster assemblies 192 and contact the floor surface in the deployed position, they cause two of the caster assemblies 192 to be lifted off the floor surface thereby shortening a wheel base of the patient support apparatus 100. A fifth wheel may also be arranged substantially in a center of the base 150.

As shown in FIG. 1, the system 10 may include an actuatable device 120 and actuators 121, 122. The actuators 121, 122 may be further defined as being capable of moving the actuatable device 120. The actuators 121, 122 may be coupled to the support structure 110 to move the patient when the patient is disposed on the patient support structure 110. In the embodiment of the patient support apparatus 100 shown in FIG. 1, the patient support apparatus 100 includes two actuators 121, 122. However, it is to be noted that the patient support apparatus 100 may include any suitable number of actuators 121, 122. Furthermore, any of the techniques described herein can utilize any number of actuators 121, 122 individually or in combination.

The actuators 121, 122 should be broadly understood as a type of motor or device that is capable of moving or controlling a mechanism or a system. For example, some suitable, non-limiting examples of the actuators 121, 122 are mechanical, hydraulic, pneumatic, electric, thermal, or magnetic actuators. The actuators 121, 122 may also include motors, such as a rotational or linear motor. In a further example, the actuators 121, 122 may include an inflation actuator. In sum, it should be understood that any type of actuator can be used in certain applications.

As described above, the actuators 121, 122 may be further defined as being capable of moving an actuatable device 120. These actuatable devices 120 are not particularly limited, and may include any device or system that includes one or more actuators 121, 122. In certain embodiments, the actuatable device 120 is one that, when actuated, results in a change of position of the patient support surfaces 141, 161 of the patient support structure 110. This change in position of one or more patient support surfaces 141, 161 when the patient occupies the patient support apparatus 100, results in a change in the position of one or more portions of the patient's body.

More specifically, in situations where a patient occupies the patient support apparatus 100, i.e., contacts one or more patient support surfaces 141, 161, operation of each of the actuatable devices 120 results in movement of one or more portions of the patient in one or more dimensions relative to a static surface, such as relative to a floor of a hospital. Examples of such movement include, but are not limited to: forward and reverse movement of the patient by virtue of movement of the patient support structure 110 along a floor; raising and lowering movement of the patient by virtue of movement of the patient support structure 110 upward and downward relative to the floor; angular movement by virtue of changing the angle of at least a portion of the patient support structure 110 relative to a floor; rotation of the patient along a longitudinal axis of the patient support structure 110 (while the patient support apparatus 100 remains stationary relative to the floor); or various combinations of those types of movement.

Without limitation, the actuatable devices 120 that result in the change of the position of one or more patient support surfaces 141, 161 of the patient support structure 110 may include a coordinated motion device, a patient raising device, a patient turning device, a patient centering device, a patient ingress/egress device, a lift device, a fowler adjustment device, a gatch adjustment device, and a transport device.

It is also contemplated that the actuatable device 120 may be of the type that does not result in a change of position, orientation, and/or elevation of the patient support surfaces 141, 161. These "non-position actuatable devices" may include, but are not limited to, a patient comfort device, such as an entertainment device, a lighting device, a temperature device, a humidity device, and an aromatherapy device, as well as patient therapy devices, such as vibration therapy devices, percussion therapy devices, compression therapy devices, patient warming devices, and electrical stimulation devices.

In FIG. 1, a therapy management system 193 is illustrated as being disposed within the footboard 182 of the patient support apparatus 100. However, in other embodiments, the therapy management system 193 may be disposed on or within the headboard 181, any of the side rails 171, 172, 173, 174, the caregiver interfaces 183, or any other suitable component of the patient support apparatus 100. Furthermore, the therapy management system 193 may be separated from the patient support apparatus 100. For example, the therapy management system 193 may be mounted to a ceiling of a hospital room, a support structure of the hospital room, or a wall of the hospital room. In further embodiments, the therapy management system 193 may be disposed within a remote computing device such as a cellular phone, a desktop computer, or a laptop.

A first input device 198 may be used by a first caregiver 195 and a second input device 199 may be used by a second caregiver 196. In the embodiment shown in FIG. 1, the input devices 198, 199 are tablet devices. The input devices 198, 199 may be mobile input devices in certain embodiments. The input devices 198, 199 may be any one of a cellular phone, a desktop computer, a nurse call station, a laptop, a wearable remote device, or any other suitable mobile input device. In other embodiments, the input devices 198, 199 may be a disposed on the patient support apparatus 100. For example, the input devices 198, 199 may be a user interface of the patient support apparatus 100 such as a touchscreen of the patient support apparatus 100, buttons of the patient support apparatus 100, or switches of the patient support apparatus 100.

It should be noted that, while the embodiment shown in FIG. 1 includes two mobile input devices 198, 199, the system 10 may include any suitable number of input devices. For example, in some embodiments, the system 10 may also include a third mobile input device for use by a third caregiver and a fourth mobile input device for use by a fourth caregiver.

Furthermore, the system 10 may be designed to be used by any suitable number of caregivers, such as a first caregiver, a second caregiver, and a third caregiver. For example, the system 10 may be used by the first caregiver 195, who may be the caregiver initially assigned to the patient or the patient's primary caregiver, and a second caregiver 196. In some embodiments, the system 10 may designate the second caregiver 196 as a backup caregiver to the first caregiver 195. In other embodiments, the second caregiver 196 may be a caregiver chosen from a group of available caregivers. The system 10 may also appoint a third, master caregiver, whom may be assigned to monitor multiple patients. For example, the third caregiver may be a nurse who is assigned to the nurse call station or who is assigned to monitor multiple patients at a local or remote command center. Of course, the system 10 may be designed for use by more than three caregivers, and include any suitable number of input devices.

The patient support apparatus 100 may include an override system 194. In FIG. 1, the override system 194 is illustrated as being disposed within the first side rail 172. However, in other embodiments, the override system 194 may be disposed on or within the headboard 181, the footboard 182, any of the side rails 171, 172, 173, 174, the caregiver interfaces 183, or any other suitable component of the patient support apparatus 100. In such embodiments, the override system 194 may include a switch, a button, a latch, a touchscreen display, a microphone, or combinations thereof. In other embodiments, the override system 194 may be separated from the patient support apparatus 100. For example, the override system 194 may be mounted to a ceiling of a hospital room, a support structure of the hospital room, or a wall of the hospital room. In another example, the override system 194 may include a remote computing device such as a cellular phone, a desktop computer, or a laptop. For instance, the mobile input devices 198, 199 may be in communication with the override system 194.

The system 10 also includes a location system 197. As shown in FIG. 1, the location system 197 may be disposed within the fourth side rail 174 of the patient support apparatus 100. However, in other embodiments, the location system 197 may be disposed on or within the headboard 181, any of the side rails 171, 172, 173, 174, the caregiver interfaces 183, or any other suitable component of the patient support apparatus 100. Furthermore, the location system 197 may include any sensor or system capable of determining location. For example, the location system 193 may include a proximity sensor, such as an infrared sensor, disposed on the footboard 182 of the patient support apparatus 100.

In other embodiments, the location system 197 may be separated from the patient support apparatus 100. For example, the location system 197 may be mounted to the ceiling of the hospital room, a support structure of the hospital room, or a wall of the hospital room. In an example embodiment, the location system 193 may include a Quick Response (QR) code scanner affixed to the wall of the hospital room, which detects a location when a QR code is scanned.

The location system 197 may include a software and/or hardware component of a computing device such as a cellular phone, a desktop computer, or a laptop. For example, the location system 197 may include a global positioning system (GPS) of the input devices 198, 199 or a wireless networking device of the input devices 198, 199. In another example, the location system 197 may include an asset tracking system, such as an RFID tracking system, installed on a server. Accordingly, any of the above-described embodiments of the location system 197 may be used to determine a location of the first input device 198, a location of the second input device 199, and/or any other input device used with system 100. When the location of an input device is determined, the location system 197 and/or the therapy management system 193 may determine the location of the associated caregiver to be the location of their respective input device.

As shown in FIG. 1, the therapy management system 193, the patient support apparatus 100, and the input devices 198, 199 may be coupled to a communication network 191 to communicate wirelessly with each other. The communication network 191 may be any suitable communication network. For example, the communication network 191 may include any one of Bluetooth, WiFi, Infrared, ZigBee, radio waves, cellular signals, any other suitable communication network, or combinations thereof. In some embodiments, the communication network 191 may include a networking device such as a gateway device, a router, or a repeater. In other embodiments, the therapy management system 193, the patient support apparatus 100, the override system 194, the location system 197, and the input devices 198, 199 may communicate using another suitable peer-to-peer, wireless, wired, or other communication protocol.

Figure 2:
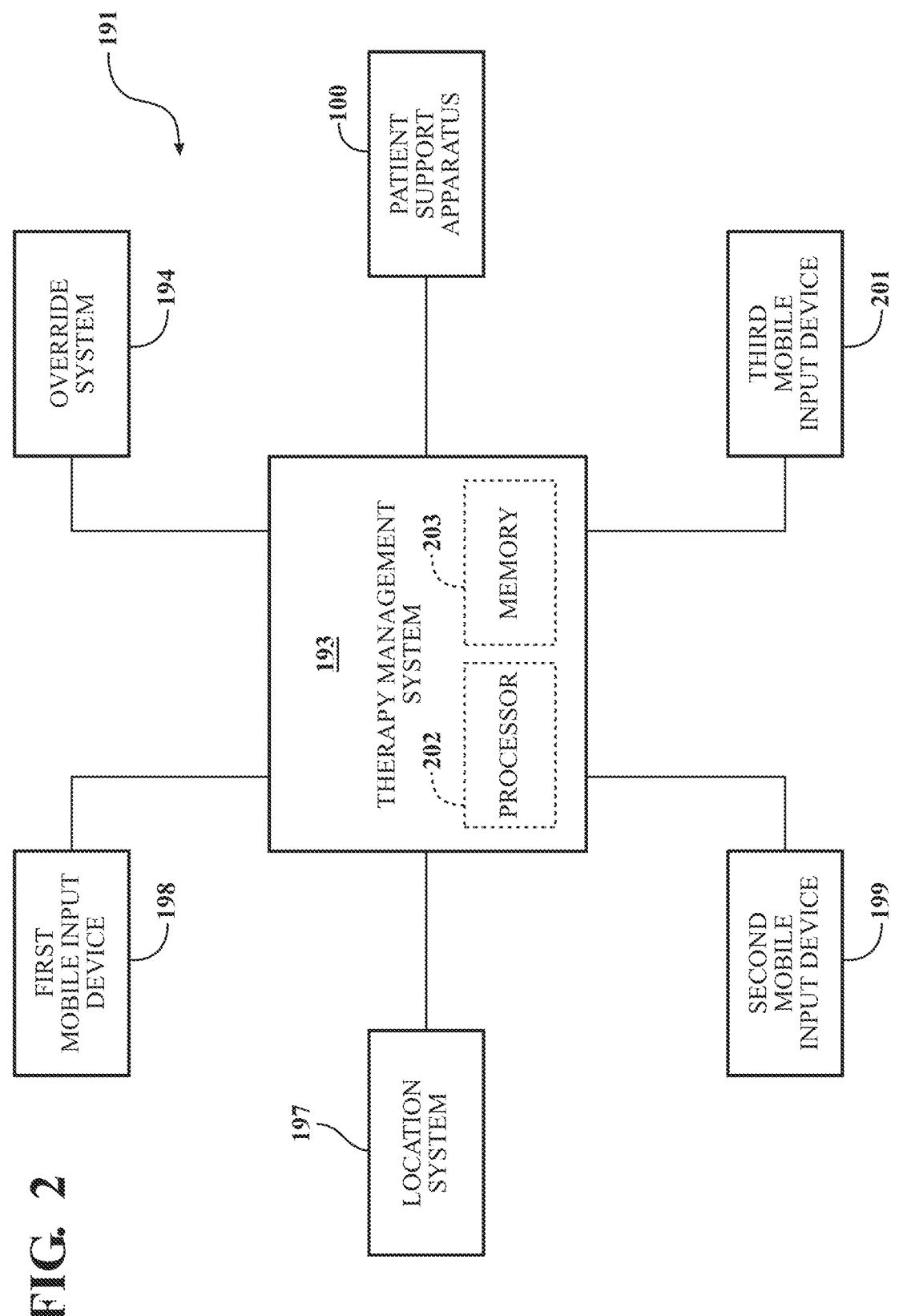
FIG. 2 is a schematic diagram illustrating the patient support apparatus, the input devices, the location system, and the therapy management system.

FIG. 2 is a schematic diagram which further illustrates the communication network 191. In the embodiment shown in FIG. 2, the therapy management system 193, the override system 194, the mobile devices 198, 199, the location system 197, and the patient support apparatus 100 may be coupled to one another via the communication network 191.

For example, as shown in FIG. 2, the therapy management system 193 may be coupled to the input devices 198, 199 via the communication network 191 and may receive a selection of a patient therapy protocol from the input devices 198, 199.

One type of therapy protocol is a default therapy protocol set according to the hospital's standard procedures for patients with specific risk profiles. Another type of therapy protocol is a variable protocol based on medical procedure data, patient characteristic data, caregiver observation data, a patient condition of the patient, a state of the patient support apparatus, the patient's preferences, medication data, prior injury data, or combinations thereof. Exemplary therapy protocols include turning protocols, pressure-ulcer risk protocols, and percussion therapy protocols.

The patient therapy protocol may include a set of desired therapeutic actions, which when executed, provide therapy to a patient. During an execution of the desired therapeutic action, the therapy management system 193 transmits a patient-moving output signal to the actuators 121, 122 of the patient support apparatus 100. The patient-moving output signal may be defined as a command which, when transmitted to the actuators 121, 122, causes movement of the one or more actuatable devices 120 that are configured to provide therapy to the patient when the patient is on the patient support apparatus 100 or other suitable therapy location. Each execution of the desired therapeutic action is termed an "instance" of the patient therapy protocol herein. For example, in one embodiment, the patient therapy protocol may cause the actuators 121, 122 to elevate the foot section of the patient support deck 140. In such an embodiment, an instance of the patient therapy corresponds to each elevation of the patient support deck 140.

An instance of the patient therapy protocol may be triggered at certain time periods, i.e., at periodic intervals, or through the occurrence of certain events. The events may be based on the medical procedure data, the patient characteristic data, the caregiver observation data, the patient condition of the patient, the state of the patient support apparatus, the patient's preferences, the medication data, the prior injury data, or combinations thereof. For example, in one embodiment, the patient therapy protocol may cause the actuators 121, 122 to elevate the foot section of the patient support deck 140 based on a periodic interval, such as every hour. In such an embodiment, the patient therapy protocol is triggered every hour. In another embodiment, the patient therapy protocol may cause the actuators 121, 122 to turn the patient based on certain events or circumstances, such as based on a risk of acquiring a pressure ulcer, which may be calculated based on a sensed moisture level of the patient support apparatus 100, an activity level of the patient, and/or a friction measurement between the patient and the patient support apparatus 100. In such an embodiment, the patient therapy protocol is triggered when the risk of acquiring a pressure ulcer exceeds a certain threshold.

The patient therapy protocol may also include a location requirement. The location requirement of a patient therapy protocol may be used to ensure that the caregiver is within a specified range of the patient support apparatus 100 before an instance of the patient therapy protocol is initiated and/or throughout a time that an instance of the patient therapy protocol is being executed. The location requirement may include a proximity to the patient support apparatus 100, a predetermined location, or combinations thereof. For instance, an "in-room" location requirement may require the caregiver to be in the hospital room of the patient support apparatus 100 during the execution of the patient therapy protocol.

For example, the location requirement may require the caregiver to be in the same wing of the hospital as the patient support apparatus 100, i.e., an "in-wing" location requirement. The location requirement may require the caregiver to be on the same floor of the hospital as the patient support apparatus, i.e., an "in-floor" location requirement. Similarly, the location requirement may require the caregiver to be in the same building of the hospital as the patient support apparatus, i.e., an "in-building" location requirement. The location requirement may also require the caregiver to be in the same functional area or department of the hospital as the patient support apparatus 100. For example, if the patient support apparatus 100 is location in the cardiology department of the hospital, the location requirement may require the caregiver to be in the cardiology department of the hospital. In other embodiments, the location requirement may require the caregiver to be adjacent to the patient support apparatus 100. In another embodiment, the location requirement may require the caregiver to be within a predetermined or programmable distance, such as 100 feet, of the patient support apparatus 100, i.e. a distance requirement. In yet another embodiment, a location score may be calculated based on the caregiver's distance from the patient support apparatus 100. In such an embodiment, the location requirement may require the caregiver to maintain a predetermined or programmable location score.

In another embodiment, the location requirement of the patient therapy protocol may inherently require the caregiver to be adjacent to the patient support apparatus 100 during the patient therapy protocol. In an example embodiment, the patient therapy protocol may require the caregiver to push a button on the patient support apparatus 100 to initiate an instance of the patient therapy protocol. In another example embodiment, the patient therapy protocol may require the caregiver to raise the side rails 171, 172, 173, 174 and confirm, using the input device of the patient support apparatus 100, that the side rails 171, 172, 173, 174 have been raised before the patient therapy protocol causes the actuators 121, 122 to turn the patient. These examples are also examples of the in-room location requirement.

Additionally, the location requirement may include a first location requirement and a subsequent location requirement, the first location requirement being the location requirement for the first instance of the selected patient therapy protocol and the subsequent location requirement being a location requirement for a subsequent instance of the patient therapy protocol. For example, in one embodiment, the location requirement of the patient therapy protocol may require the caregiver to be in-room when the caregiver initiates the first instance of the patient therapy protocol, and may require that the caregiver be located within a certain predetermined or programmable distance of patient support apparatus, such as 100 feet, during subsequent instances of the patient therapy protocol. In such an embodiment, the location requirement includes a first location requirement and a subsequent distance requirement.

Furthermore, the therapy management system 193 may determine the location requirement of the patient therapy protocol based on the medical procedure data, the patient characteristic data, the caregiver observation data, the patient condition of the patient, the state of the patient support apparatus, a risk level of the patient therapy protocol, the patient's preferences, the medication data, the prior injury data, or combinations thereof.

In embodiments where the therapy management system 193 determines the location requirement of the patient therapy protocol based on the medical procedure data, the medical procedure data may include a type of medical procedure undergone by the patient, a duration since a last medical procedure undergone by the patient, a duration since admittance of the patient to a caregiving facility, or combinations thereof. In an example embodiment, the location requirement may require the caregiver to be in-room if the patient has recently undergone back surgery based on the medical procedure data and if the patient therapy protocol causes the actuators 121, 122 to incline the back section of the patient support deck 140.

In embodiments where the therapy management system 193 determines the location requirement of the patient therapy protocol based on the patient characteristic data, the patient characteristic data may include a height of the patient, fall risk data, width of the patient, age of the patient, weight of the patient, body mass index of the patient, or combinations thereof. In an example embodiment, the location requirement may require the caregiver to be in-room if the patient has a high fall risk based on the fall risk data and if the patient therapy protocol causes the actuators 121, 122 to turn the patient.

In embodiments where the therapy management system 193 determines the location requirement of the patient therapy protocol based on the caregiver observation data, the caregiver observation data may include psychological data of the patient, phobia data of the patient, pain sensitivity data of the patient, nausea data of the patient, or combinations thereof. In an example embodiment, the location requirement may require a caregiver to be in-room if the patient is experiencing nausea symptoms based on the nausea data and if the therapy protocol causes movement of the patient's head.

In embodiments where the therapy management system 193 determines the location requirement of the patient therapy protocol based on the patient condition, the patient condition may include physiological data of the patient such as a heart rate of the patient, a temperature of the patient, vital signs of the patient, a comfort level of the patient, a pain rating of the patient, a position of the patient, or a blood pressure of the patient. In an example embodiment, the location requirement may require the caregiver to be in-room if the heart rate of the patient is at a high-level.

In embodiments where the therapy management system 193 determines the location requirement of the patient therapy protocol based on the state of the patient support apparatus, the state of the patient support apparatus may include a height of a component of the patient support apparatus 100, a length of a component of the patient support apparatus 100, a position of a component of the patient support apparatus 100, a state of a component of the patient support apparatus 100, a velocity of a component of the patient support apparatus 100, an acceleration of a component of the patient support apparatus 100, or combinations thereof. In an example embodiment, the location requirement may require the caregiver to be adjacent to the patient support apparatus 100 before the patient therapy protocol causes the actuators 121, 122 to move the patient if the side rails 171, 172, 173, 174 are in the lowered position.

In embodiments where the therapy management system 193 determines the location requirement of the patient therapy protocol based on the risk level of the patient therapy protocol, the patient therapy protocol may be categorized as a low-risk patient therapy protocol, a medium-risk patient therapy protocol, or a high-risk patient therapy protocol. For example, in one embodiment, a patient therapy protocol which causes the actuators 121, 122 to turn the patient may be categorized as a high-risk patient therapy protocol and a patient therapy protocol which causes the actuators 121, 122 to incline the foot section of the patient support deck 140 may be categorized as a low-risk patient therapy protocol. In such an embodiment, the location requirement of the high-risk patient therapy protocol may require the caregiver to be adjacent to the patient support apparatus 100 whereas the location requirement of the low-risk patient therapy protocol may require the caregiver to be in-wing. Of course, it should be noted that the patient therapy protocol may be categorized as a low-risk patient therapy protocol, a medium-risk patient therapy protocol, or a high-risk patient therapy protocol based on the medical procedure data, the patient characteristic data, the patient condition, the state of the patient support apparatus, the patient's preferences, the medication data, the prior injury data, or combinations thereof.

Similarly, the therapy management system 193 may determine the location requirement based on the patient's preferences, the medication data, and/or the prior injury data. In an example embodiment, the location requirement may be in-room to for each instance of the patient therapy protocol if the patient has recently suffered a knee injury and if the patient therapy protocol is of a type that would cause the actuators 121, 122 to move the patient's knee.

It should be noted that the therapy management system 193 may receive the medical procedure data, the patient characteristic data, the patient condition, the state of the patient support apparatus, the medication data, and the prior injury data in a variety of ways. In one embodiment, the caregiver or the patient may supply the above data, states, and conditions to the therapy management system 193. In further embodiments, the caregiver or the patient may supply the data, states, and conditions to the controller 195 via the input devices 198, 199. In still other embodiments, the therapy management system 193 may receive the data, states, and conditions from a database such as an electronic medical record or from sensors connected to or included within the therapy management system 193.

Furthermore, as shown in FIG. 2, the therapy management system 193 includes a memory 203 and a processor 202, which may be used for storing and processing the medical procedure data, the patient characteristic data, the patient condition, the state of the patient support apparatus, the patient's preferences, the medication data, and the prior injury data. The processor 202 may be any processor suitable for processing data. For example, the processor 202 may be a processor typically found in a desktop computer or a processor typically found in a mobile processing device such as a cellular phone, a tablet, or a laptop. Similarly, the memory 203 may be any memory suitable for storage of data and computer-readable instructions. For example, the memory 203 may be a local memory, an external memory, or a cloud-based memory embodied as random access memory (RAM), non-volatile RAM (NVRAM), flash memory, or any other suitable form of memory.

The location requirement may also vary for different patient therapy protocols. As noted above, the patient therapy protocol may depend on a variety of factors, including the medical procedure data, the patient characteristic data, the caregiver observation data, the patient condition of the patient, the state of the patient support apparatus, the risk level of the patient therapy protocol, the patient's preferences, the medication data, the prior injury data, or combinations thereof. For example, as previously discussed, the location requirement may differ between two different patient therapy protocols based on the risk level of the two different patient therapy protocol.

Furthermore, whether the location requirement is used to ensure that the caregiver is within a specified range of the patient support apparatus 100 before an instance of the patient therapy protocol is initiated or throughout a time that an instance of the patient therapy protocol is executed may also be based on the medical procedure data, the patient characteristic data, the caregiver observation data, the patient condition of the patient, the state of the patient support apparatus, the patient's preferences, the medication data, the prior injury data, or combinations thereof. For example, in a more urgent situation, such as a situation where the vital signs of the patient indicate that the patient may enter cardiac arrest, the location requirement may be enforced throughout an instance of the patient therapy protocol, at periodic intervals, such as every 5 minutes. Conversely, if the patient is in a stable condition, the location requirement may only be enforced before initiating an instance of the patient therapy protocol.

As shown in FIG. 2, the therapy management system 193 may be coupled to the input devices 198, 199 via the communication network 191 and may be configured to transmit a notification signal to the input devices 198, 199. The notification signal may cause the input devices 198, 199 to display a text or graphic display, illuminate an external light, activate an audible alarm, vibrate, and/or generate any other suitable notification.

It should be appreciated that, in some embodiments, the therapy management system 193 may be coupled to the input devices 198, 199 without the communication network 191. For example, in an embodiment where the input devices 198, 199 are the user interface of the patient support apparatus 100 and the therapy management system 193 is disposed within the patient support apparatus 100, the input devices 198, 199 may be in direct communication with the therapy management system 193. As such, the therapy management system 193 may receive the selection of the patient therapy protocol 100 and transmit the notification signal to the input devices 198, 199 without the communication network 191.

Additionally, the therapy management system 193 may be coupled to the location system 197 and may receive a location input signal from the location system 197. As shown in FIG. 2, the therapy management system 193 may be coupled to the location system 197 via the communication network 191. As such, the therapy management system 193 is able to receive the location input signal even if the therapy management system 193 is not in direct communication with the location system 197. For example, in the previously stated embodiment where the location system 193 includes the GPS of the first input device 198, the therapy management system 193 may receive the location input signal from the GPS of the first input device 198 via a cellular signal or via a WiFi connection.

In some embodiments, the therapy management system 193 may be coupled to the location system 197 without the communication network 191. For example, in the embodiment shown in FIG. 1, the location system 197 and the therapy management system 193 are disposed within the patient support apparatus 100. In such an embodiment, the location system 197 and the therapy management system 193 may be in direct communication with each other. As such, the therapy management system 193 may receive the location input signal from the location system 197 without the use of the communication network 191.

Also shown in FIG. 2, the therapy management system 193 may be coupled to the patient support apparatus 100. In this way, the therapy management system 193 may transmit the patient-moving output signal to the actuators 121, 122 of the patient support apparatus 100 to cause movement of the one or more actuatable devices 120. As shown in FIG. 2, the therapy management system 193 may be coupled to the patient support apparatus 100 via the communication network 191. In such an embodiment, the patient support apparatus 100 may transmit the patient-moving output signal to a controller of the patient support apparatus 100 via the communication network 191. The controller of the patient support apparatus 100 may then transmit the patient-moving output signal to the actuators 121, 122 of the patient support apparatus 100. For example, in the previously stated embodiment where the therapy management system 193 may be mounted to a ceiling of a hospital room, the therapy management system 193 may use the hospital's WiFi connection to transmit the patient-moving output signal to the controller of the patient support apparatus 100. In this way, the therapy management system 193 is able to cause one or more actuatable devices 120 of the patient support apparatus 100 to move the patient, even if the therapy management system 193 is separated from the patient support apparatus 100.

In some embodiments, the therapy management system 193 may be coupled to the patient support apparatus 100 without the communication network 191. For example, in the embodiment shown in FIG. 1, the therapy management system 193 is disposed within the patient support apparatus 100. In such an embodiment, the therapy management system 193 may transmit the patient-moving output signal directly to a controller of the patient support apparatus 100 to initiate the selected patient therapy protocol without the communication network 191. In another such embodiment, the therapy management system 193 may transmit the patient-moving output signal directly to the actuators 121, 122 of the patient support apparatus 100 without the communication network 191.

Additionally, the therapy management system 193 may be coupled to the override system 194 and may receive a control signal from the override system 194. As shown in FIG. 2, the therapy management system 193 may be coupled to the override system 194 via the communication network 191. In such an embodiment, the override system 194 may transmit the control signal to the therapy management system 193 via the communication network 191. For example, in the previously stated embodiment where the override system 194 is in communication with the input devices 198, 199, the therapy management system 193 may receive the control signal via a cellular signal or via a WiFi connection.

However, in other embodiments, the therapy management system 193 may be coupled to the override system 194 without the communication network 191. For example, in an embodiment where the override system 194 is a touchscreen display disposed on the patient support apparatus 100 and the therapy management system 193 is disposed within the patient support apparatus 100, the override system 194 and the therapy management system 193 may be in direct communication with each other. As such, the therapy management system 193 may receive the control signal without the communication network 191.

As described above, the override system 194 may transmit the control signal to the therapy management system 193. In some embodiments, the control signal may be an acceptance of the patient therapy protocol, a denial of the patient therapy protocol, a modification to the patient therapy protocol, a selection of a different patient therapy protocol, or combinations thereof. In this way, the override system 194 allows a caregiver to immediately adjust the patient therapy protocol if necessary.

Figure 3A:
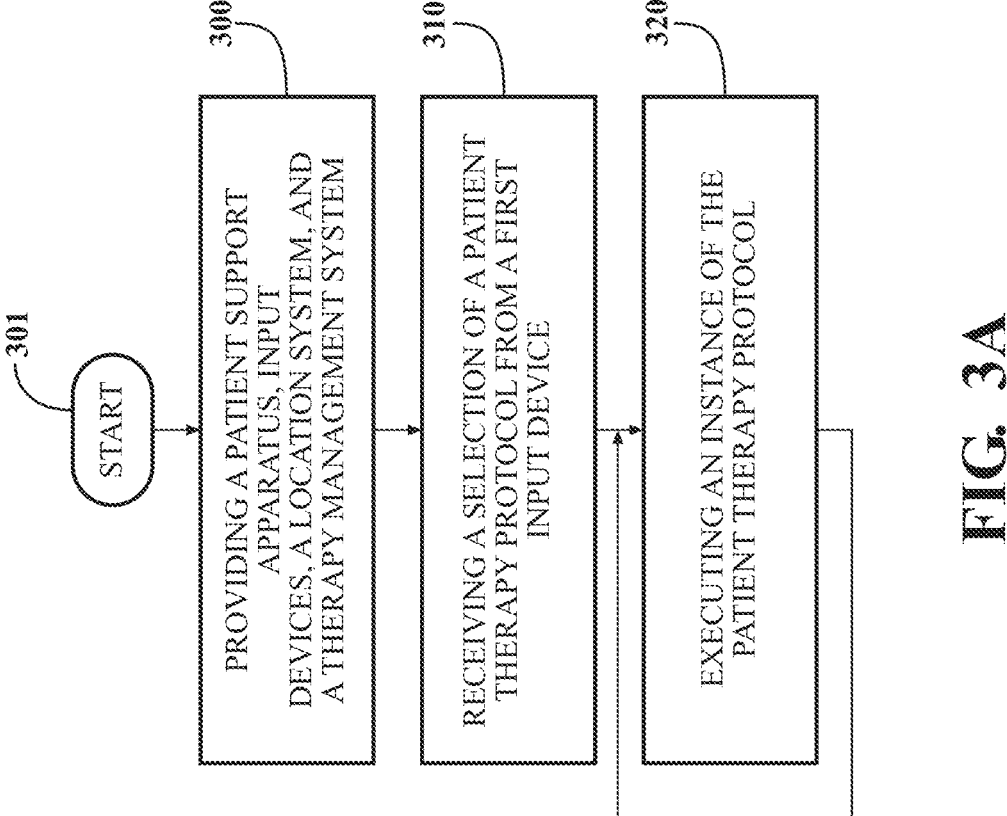
FIG. 3A is a flowchart illustrating a first embodiment of a method of managing patient therapy protocols, which includes a step of executing an instance of the patient therapy protocol.

To further aid in understanding the system 10 for managing patient therapy protocols, FIG. 3A provides a flow-chart illustrating a method of managing patient therapy protocols, which may be executed by the therapy management system 193. As shown in FIG. 3A, the method includes a step 300 of providing the patient support apparatus 100, the input devices 198, 199, the location system 197, and the therapy management system 193. The method also includes a step 310 of receiving a selection of the patient therapy protocol from the first input device 198 and a step 320 of executing an instance of the patient therapy protocol.

An example embodiment is used herein to further explain the method. The selected patient therapy protocol received during step 310 may, when executed, cause the actuators 121, 122 to elevate the foot section of the patient support deck 140 every hour for five hours. During step 320, the method may execute an instance of the selected patient therapy protocol and elevate the foot section of the patient support deck 140. This embodiment is referred to herein as the "the foot elevation embodiment".

Figure 3B:
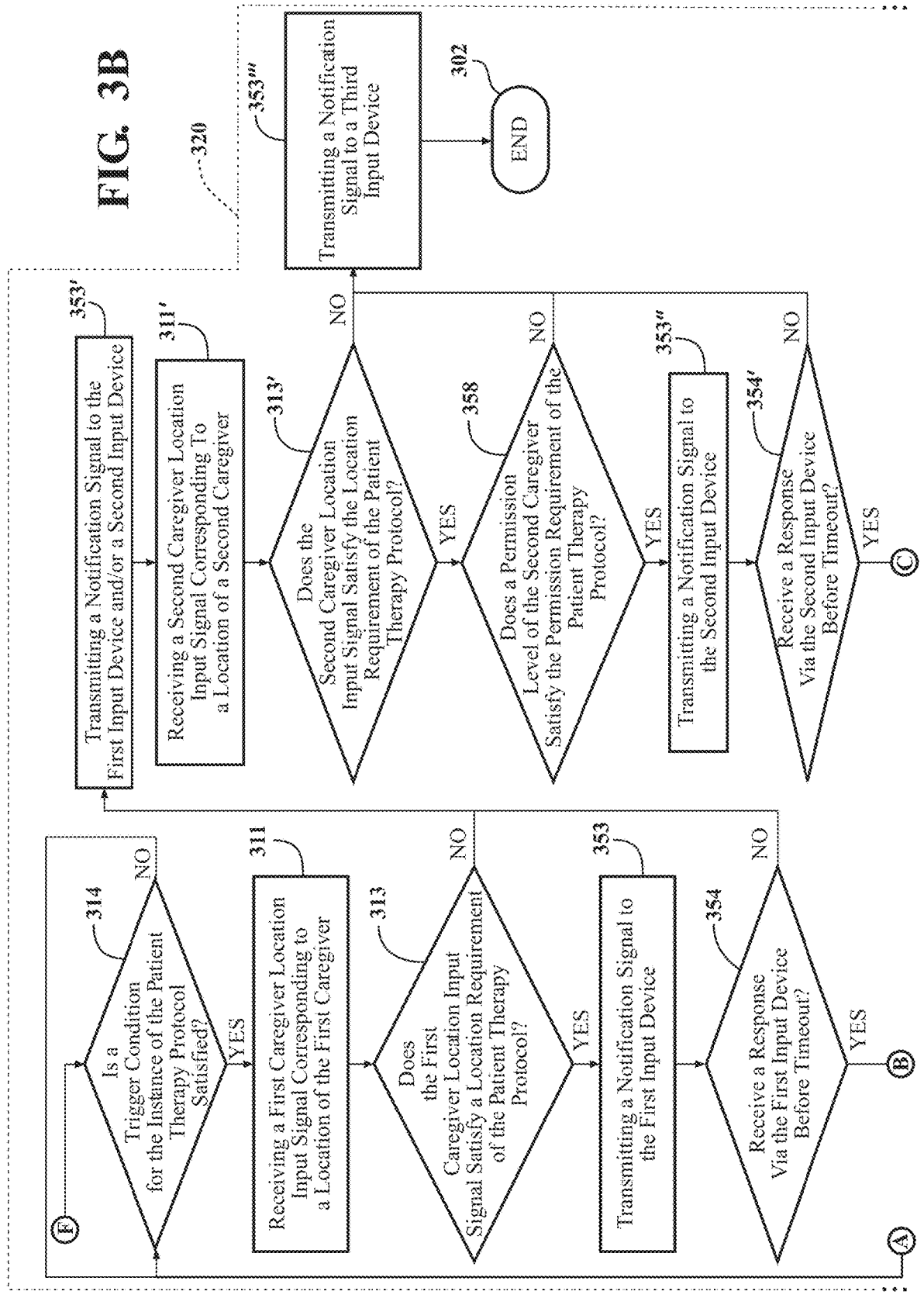
FIG. 3B is a flowchart illustrating the step of executing the instance of the patient therapy protocol.

Step 320 is further illustrated in FIG. 3B. As shown, the method includes a step 314 of determining whether a trigger condition for the instance of the patient therapy protocol is satisfied. If the trigger condition is satisfied, the method continues to a next step and may eventually execute the instance of the patient therapy protocol. If the trigger condition is not satisfied, the method proceeds in a loop and continues determining whether the trigger condition for the instance of the patient therapy protocol is satisfied.

During step 314, the method may determine whether the trigger condition for the instance of the patient therapy protocol is satisfied based on an amount of time. In the foot elevation embodiment, the method, during step 314, determines whether an hour has passed since the last instance of the patient therapy protocol or since the patient therapy protocol was selected during step 310. If an hour has passed, the trigger condition for the instance of the patient therapy protocol is satisfied.

In another embodiment of step 314, the method may determine whether to execute the first instance of the patient therapy protocol based on a sensed parameter. For example, in the embodiment where the patient therapy protocol causes the actuators 121, 122 to turn the patient based on the risk of acquiring a pressure ulcer, the method may receive the sensed moisture level of the patient support apparatus 100, the activity level of the patient, and/or the friction measurement between the patient and the patient support apparatus 100 and calculate the risk of acquiring a pressure ulcer during step 314. In such an embodiment, if the risk of acquiring a pressure ulcer exceeds a certain threshold, the trigger condition is satisfied.

In other embodiments of step 314, the method may determine whether the trigger condition for the patient therapy protocol is satisfied based on determining whether the selected patient therapy protocol is an allowable patient therapy protocol. The method may determine whether the selected patient therapy protocol is an allowable patient therapy protocol based on the medical procedure data, the patient characteristic data, the caregiver observation data, the patient condition of the patient, the state of the patient support apparatus, the patient's preferences, the medication data, the prior injury data, or combinations thereof. For example, in an embodiment where the patient therapy protocol causes the actuators 121, 122 to turn the patient, the method may determine whether the trigger condition is satisfied based on whether the side rails 171, 172, 173, 174 of the patient support apparatus 100 are in the raised position. In an embodiment where patient therapy protocol causes the actuators 121, 122 to incline the back section of the patient support deck 140, the method may determine whether the trigger condition is satisfied based on whether patient has recently undergone back surgery.

It should be appreciated that the method may exit step 314 before determining whether an instance of the patient therapy protocol should be executed. In one embodiment, the method may wait a predetermined or programmable amount of time before exiting step 314. For example, the method may exit step 314 if the method has not determined whether an instance of the patient therapy protocol should be executed after 6 hours. In another embodiment, the method may exit step 314 if the caregiver aborts the patient therapy protocol. For example, in one embodiment, the method may exit step 314 if the caregiver denies the patient therapy protocol using the override system 194.

As shown in FIG. 3B, after determining that the first instance of the patient therapy protocol should be executed, the method proceeds to a step 311 of receiving a first caregiver location input signal corresponding to a location of the first caregiver 195. The method then proceeds to a step 313 of determining whether or not the first caregiver location input signal satisfies the location requirement of the selected patient therapy protocol. In the foot elevation embodiment, the location requirement of the selected patient therapy protocol may require a caregiver to be in the same room as the patient support apparatus 100 when the foot section of the patient support deck 140 is being elevated. As such, the method may, in the foot elevation embodiment, receive the location of the first caregiver 195 during step 311 and determine whether the first caregiver 195 is in the same room as the patient support apparatus 100.

If the first caregiver location input signal satisfies the location requirement of the selected patient therapy protocol, the method may proceed to a step 353 of transmitting a notification signal to the first input device 198. During step 353, the method transmits the notification signal to the first input device 198 to notify the first caregiver 195 of the instance of the patient therapy protocol.

Once the first caregiver 195 is notified of the instance of the patient therapy protocol, the method may proceed to a step 354 of receiving a response to notifying the first caregiver 195 of the selected patient therapy protocol via the first input device 198. The response received during step 354 may include an acceptance of the instance of the patient therapy protocol, a denial of the instance of the patient therapy protocol, a modification to the instance of the patient therapy protocol, a selection of a different patient therapy protocol, or combinations thereof. For example, in the foot elevation embodiment, the first caregiver 195 may, via the first input device 198, accept an elevation of the foot section of the patient support deck 140, deny the elevation of the foot section of the patient support deck 140, modify the patient therapy protocol so that the thigh section of the patient support deck 140 is elevated instead, or select a patient therapy protocol which causes the actuators 121, 122 to turn the patient.

Figure 3C:
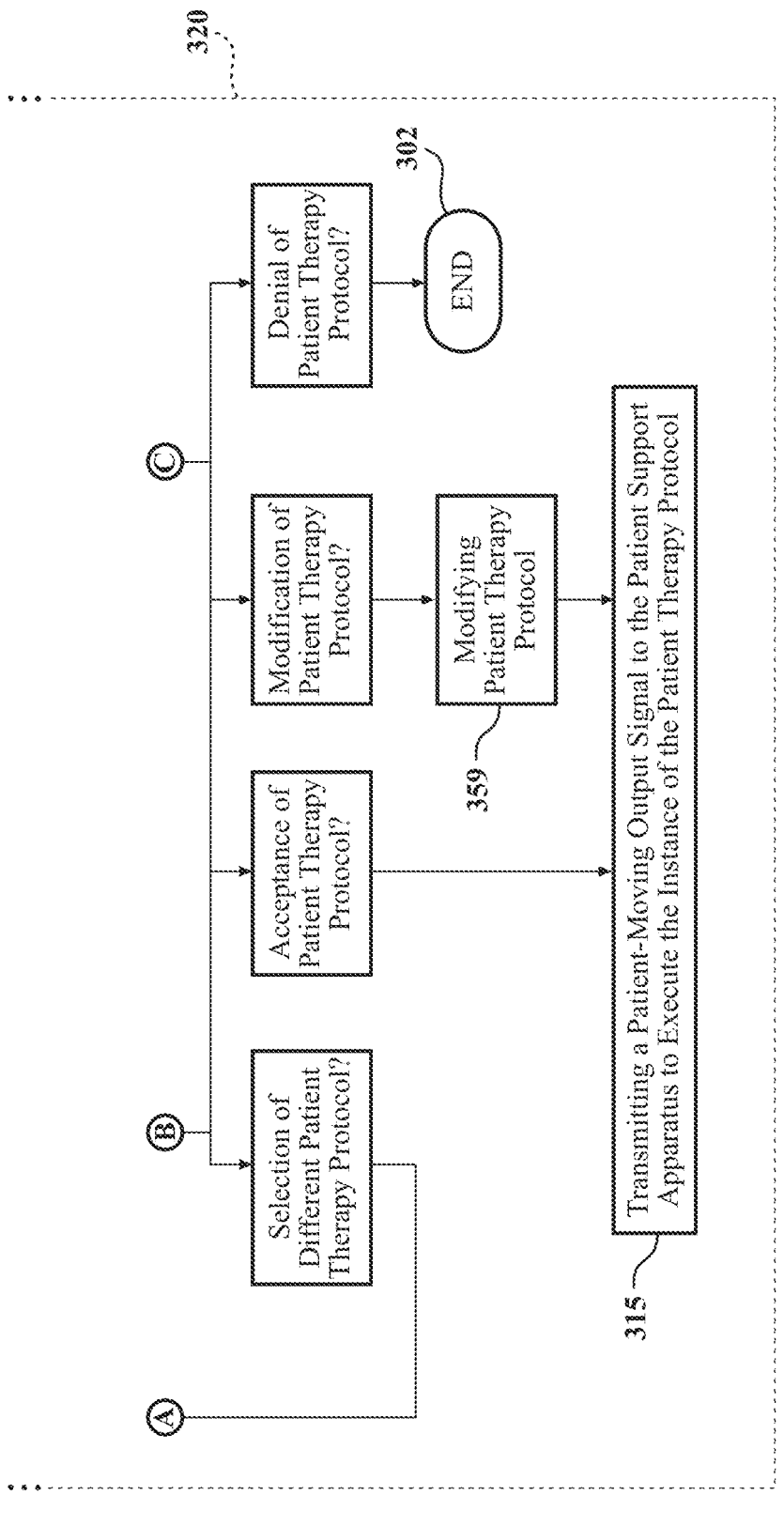
FIG. 3C is a flowchart further illustrating the step of executing the instance of the patient therapy protocol.

FIG. 3C provides a flowchart illustrating the step 320 if the method receives the response during step 354. If the response received during step 354 is the acceptance of the instance of the patient therapy protocol, the method proceeds to a step 315 of transmitting the patient-moving output signal to the patient support apparatus 100 to execute the instance of the selected patient therapy protocol, as shown in FIG. 3C. In the foot elevation embodiment, if the first caregiver 195 accepts the patient therapy protocol, the patient-moving output signal is transmitted and the foot section of the patient support deck 140 is elevated.

However, if the response received during step 354 is the denial of the instance of the patient therapy protocol, the modification to the instance of the patient therapy protocol, or the selection of a different patient therapy protocol, the method may proceed differently. For example, if the response received during step 354 is the denial of the instance of the patient therapy protocol, the method may proceed to step 302, or an end of the method. During step 302, the method may reposition the patient support apparatus 100 back to its initial state and return to step 301, a start of the method.

If the response received during step 354 is the modification to the instance of the patient therapy protocol, the therapy management system 193 may modify the patient therapy protocol during step 359 before proceeding to step 315 to execute the modified patient therapy protocol. If the response received during step 354 is the selection of the different patient therapy protocol, the method may return to step 314 and determine whether or not to execute the first instance of the different patient therapy protocol.

Furthermore, during step 354, the method may wait a predetermined or programmable amount of time for the response to notifying the first caregiver 195. If the method does not receive the response to notifying the first caregiver 195 within the predetermined or programmable amount of time, the method may timeout and proceed to a step 353' of transmitting a notification signal to the first input device 198 and/or the second input device 199 to notify the first caregiver 195 and/or the second caregiver 196 that the method did not receive the response from the first caregiver 195 within the predetermined or programmable amount of time. In other embodiments, the method may proceed to step 302, the end of the method, if the method does not receive the response from the first caregiver 195 within the predetermined or programmable amount of time.

In some embodiments, depending on the type of the patient therapy protocol, the method may proceed to step 315 and execute the instance of the patient therapy protocol even if the method does not receive the response from the first caregiver 195. In such embodiments, the method may execute the instance of the patient therapy protocol for a period of time, such as five minutes, before proceeding to step 353'. The method may also continue waiting for the response from the first caregiver 195 while executing the patient therapy protocol for the period of time.

Similarly, if the location of the first caregiver 195 does not satisfy the location requirement of the patient therapy protocol during step 313, the method may also proceed to step 353'. Here, however, the method transmits a notification signal to the first input device 198 and/or the second input device 199 to notify the first caregiver 195 and/or the second caregiver 196 that the location of the first caregiver 195 does not satisfy the location requirement of the patient therapy protocol.

Furthermore, if the first caregiver location input signal does not satisfy the location requirement of the selected patient therapy protocol, the method may proceed to step 311' and step 313'. Step 311' is similar to step 311 because, during both steps, the method receives a location input signal corresponding to a location of a caregiver. However, during step 311', the method receives a second caregiver location input signal corresponding to a location of the second caregiver 196. Similarly, step 313' is similar to step 313 because, during both steps, the method determines whether the caregiver location input signal satisfies the location requirement of the patient therapy protocol. However, during step 313', the method determines whether or not the second caregiver location input signal satisfies the location requirement of the selected patient therapy protocol. In the foot elevation embodiment, the method first receives the location of the second caregiver 196 during step 311'. The method may then determine whether the second caregiver 196 is in the same room as the patient support apparatus 100 during step 313'.

If the second caregiver location input signal does not satisfy the location requirement of the selected patient therapy protocol, the method may proceed to step 302, the end of the method. However, in some embodiments, such as the embodiment shown in FIG. 2, the system 10 may include a third input device 201 for a third caregiver. In such embodiments, the method may first proceed to a step 353''' where the method transmits a notification signal to the third input device 201 to notify the third caregiver that the second caregiver location input signal does not satisfy the location requirement of the selected patient therapy protocol. As shown in FIG. 3B, the method may then proceed to step 302, the end of the method.

If the second caregiver location input signal does satisfy the location requirement of the selected patient therapy protocol during step 313', the method may then proceed to a step 358 of determining whether a permission level of the second caregiver 199 satisfies a permission requirement of the selected patient therapy protocol. In some embodiments, the permission level of the caregiver may be based on a hospital hierarchy. For example, the permission level of the caregiver may be based on whether the caregiver is a nurse, a medical intern, a medical student, a physician assistant, a resident, a doctor, or a surgeon. In other embodiments, the permission level of the caregiver may be based on a floor or unit of the hospital. For example, the permission level may require the caregiver to be assigned to the same floor or unit of the hospital as the patient. In the foot elevation embodiment, the selected patient therapy protocol may require that the caregiver be a nurse, a doctor, or a medical intern. As such, the method, during step 358, determines whether the second caregiver 196 is a nurse, a doctor, or a medical intern.

If the permission level of the second caregiver 196 does not satisfy the permission requirement of the selected patient therapy protocol, the method may notify the third caregiver that the second caregiver 196 does not satisfy the permission requirement of the selected patient therapy protocol during step 353''' before proceeding to the end of the method.

If the permission level of the second caregiver 196 satisfies the permission requirement of the selected patient therapy protocol, the method may proceed to step 353". During step 353", the method may notify the second caregiver 196 of the instance of the patient therapy protocol and that the second caregiver 196 satisfies both the permission requirement and the location requirement of the selected patient therapy protocol.

As shown in FIG. 3B, the method may then proceed to step 354'. Step 354' is similar to step 354 because, during both steps, the method determines whether a response to notifying a caregiver has been received. Furthermore, during both steps, the method may receive the acceptance of the instance of the patient therapy protocol, the denial of the instance of the patient therapy protocol, the modification to the instance of the patient therapy protocol, the selection of a different patient therapy protocol, or combinations thereof, and proceed as previously discussed and shown in FIG. 3C. However, during step 354', the method receives a response to notifying the second caregiver 196 via the second input device 199. If the response received during step 354' is the acceptance of the instance of the patient therapy protocol, the method proceeds to a step 315 of transmitting the patient-moving output signal to the patient support apparatus 100 to execute the instance of the selected patient therapy protocol, as shown in FIG. 3C.

Furthermore, it should be noted that, during step 354', the method may timeout and proceed to step 353''' if the method does not receive the response to notifying the second caregiver 196 within a predetermined or programmable amount of time. During step 353''', the method may transmit a notification signal to the third input device 201 to notify the third caregiver that the method did not receive the response from the second caregiver 196 within the predetermined or programmable amount of time.

In other embodiments, the method may proceed to step 315 even if the method does not receive the response to notifying the second caregiver 196 during step 354'. In such embodiments, the method may execute the instance of the patient therapy protocol for a period of time, such as five minutes, before proceeding to step 353''' and step 302, the end of the method. The method may also continue waiting for the response from the second caregiver 196 while executing the patient therapy protocol for the period of time.

Referring now back to FIG. 3A, once the method completes step 320, the method returns to the beginning of step 320 to execute another instance of the patient therapy protocol. The method repeats step 320 in accordance with the selected patient therapy protocol. For example, in some embodiments, the method may repeat step 320 for a predetermined or programmable number of instances. In another embodiment, the method may repeat step 320 for a predetermined or programmable amount of time. In yet another embodiment, the method may repeat step 320 until the caregiver ends the method. In other embodiments, the method may repeat step 320 based on the medical procedure data, the patient characteristic data, the caregiver observation data, the patient condition of the patient, the state of said patient support apparatus, the risk level of the selected patient therapy protocol, the patient's preferences, the medication data, the prior injury data, or combinations thereof. In the foot elevation embodiment, the selected patient therapy protocol received during step 310 causes the actuators 121, 122 to elevate the foot section of the patient support deck 140 every hour for five hours. Therefore, in the foot elevation embodiment, step 320 is repeated five times.

It should be noted that, in the embodiment of the method shown in FIGS. 3A and 3B, the method determines whether the location of the caregiver satisfies the location requirement of the selected patient therapy protocol before transmitting the patient-moving output signal to the patient support apparatus 100 to execute an instance of the selected patient therapy protocol. In other embodiments of the method, the method may also determine whether the location of the caregiver satisfies the location requirement of the selected patient therapy protocol throughout a time that an instance of the selected patient therapy protocol is executed. For example, the method may, in the foot elevation embodiment, require the caregiver to be in the same room as the patient support apparatus 100 while the foot section of the patient support deck 140 is being elevated.

Figure 4A:
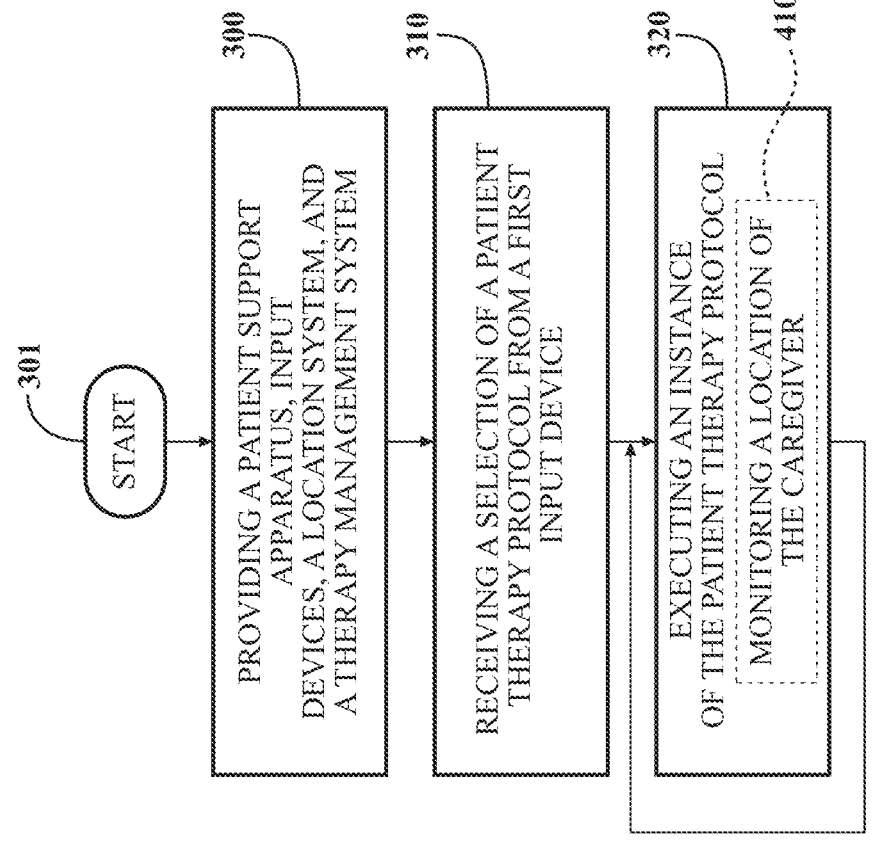
FIG. 4A is a flowchart illustrating a second embodiment of the method of managing patient therapy protocols, which includes a step of monitoring a location of a caregiver.

FIG. 4A provides a flowchart illustrating an embodiment where the method determines whether the location of the caregiver satisfies the location requirement of the selected patient therapy protocol throughout a time that an instance of the selected patient therapy protocol is executed. Just as the method shown in FIG. 3A included step 300, step 310, and 320, the method shown in FIG. 4A also includes step 300, step 310, and step 320. However, as shown in FIG. 4A, step 320 includes a step 410 of monitoring the location of the caregiver. As such, the method monitors the location of the caregiver throughout the time that the instance of the patient therapy protocol is executed.

Figure 4B:
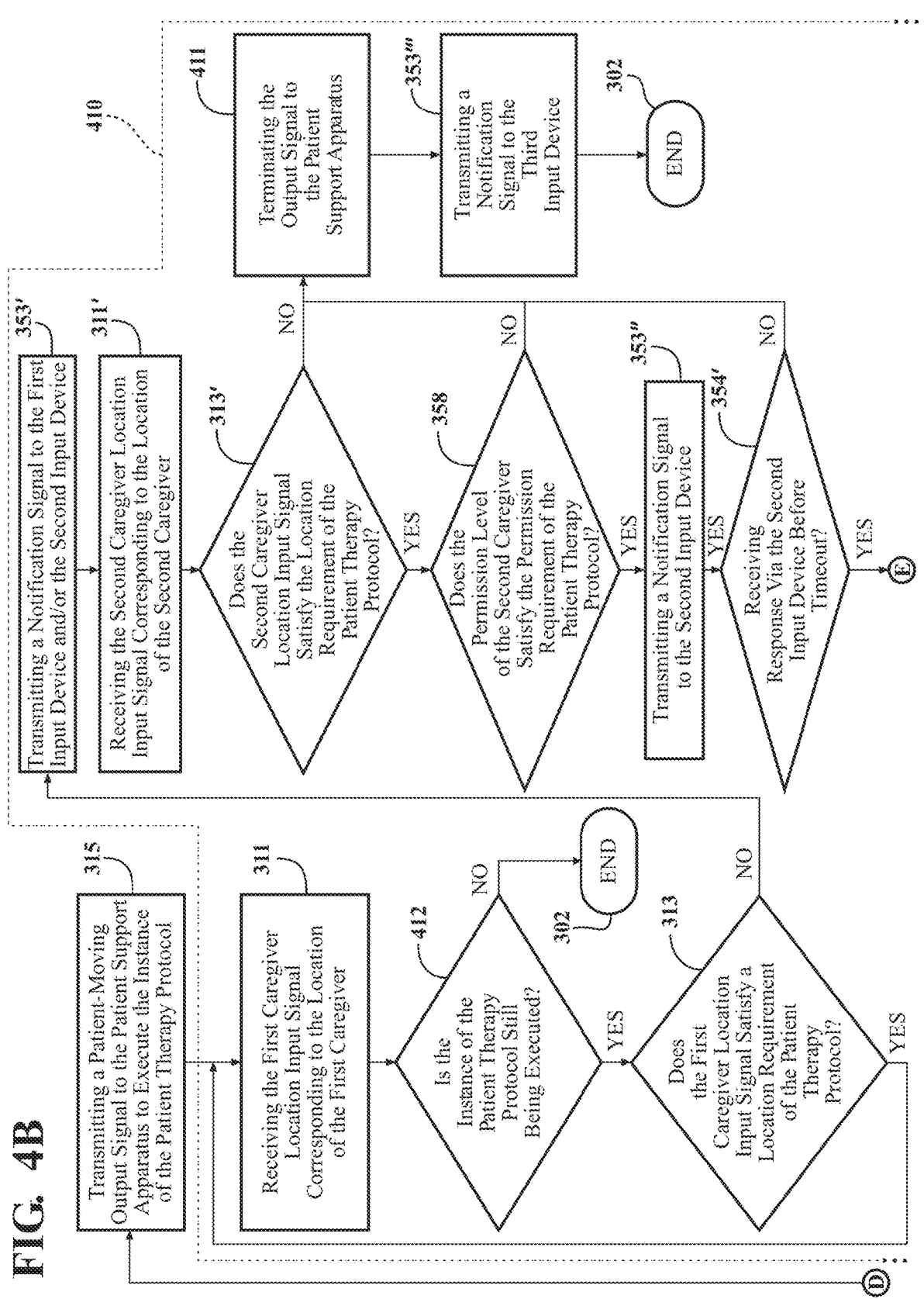
FIG. 4B is a flowchart illustrating the step of monitoring the location of the caregiver.

FIG. 4B provides a flowchart further illustrating step 410. As shown in FIG. 4A, step 410 begins after the method transmits the patient-moving output signal to the patient support apparatus 100 to execute the instance of the patient therapy protocol during step 315. As such, it should be understood that step 410 occurs while the method is executing the instance of the patient therapy protocol. In the foot elevation embodiment, step 410 occurs while the foot section of the patient support deck 140 is being elevated.

As shown in FIG. 4B, step 410 shares some of the same steps as step 320, as shown in FIG. 3B. For example, steps 311, 311', 313, 313', 315, 353', 353'', 353''', 354', and 358 are all included in step 410 and have all been discussed in the previous discussion of step 320. Step 410 does, however, deviate from step 320 in some regards.

For example, while step 320 of FIG. 3B begins with step 314, the step of determining whether or not to execute the instance of the patient therapy protocol, step 410 of FIG. 4B begins by receiving the first caregiver location input signal corresponding to the location of the first caregiver 195 during step 311. This is because step 410 occurs while the method is executing the instance of the patient therapy protocol. In the foot elevation embodiment, the location of the caregiver 195 is received during step 311 while the foot section of the patient support deck 140 is being elevated.

After the method receives the first location input signal during step 311, the method may determine whether the instance of the patient therapy protocol is still being executed during a step 412. In the foot elevation embodiment, the method determines whether the foot section of the patient support deck 140 is still being elevated during step 412. If the instance of the patient therapy protocol is no longer being executed, the method proceeds to step 302, the end of the method. However, if the instance of the patient therapy protocol is still being executed, the method may proceed to step 313, where the method determines if the first caregiver location input signal satisfies the location requirement of the patient therapy protocol. If the first caregiver location input signal satisfies the location requirement, the method may repeat step 311 to again receive the first caregiver location input signal. Otherwise, the method may proceed to step 353', step 311', step 313', etc. as the method does during step 320 of the method.

Furthermore, because the instance of the patient therapy protocol is being executed during step 410, step 410 includes a step 411 of terminating the patient-moving output signal to the patient support apparatus 100. As shown in FIG. 4B, if the method determines that the second caregiver location input signal does not satisfy the location requirement of the selected patient therapy protocol, if the method determines that the permission level of the second caretaker 196 does not satisfy the permission requirement of the patient therapy protocol, or if the method does not receive a response during step 354', the method may proceed to step 411 and terminate the patient-moving output signal to cease execution of the selected patient therapy protocol before ultimately proceeding to step 302, the end of the method. In the foot elevation embodiment, terminating the patient-moving output signal during step 411 would cease the elevation of the foot section of the patient support deck 140. The method may then lower the foot section of the patient support deck 140 to its initial position during step 302, the end of the method.

Figure 4C:
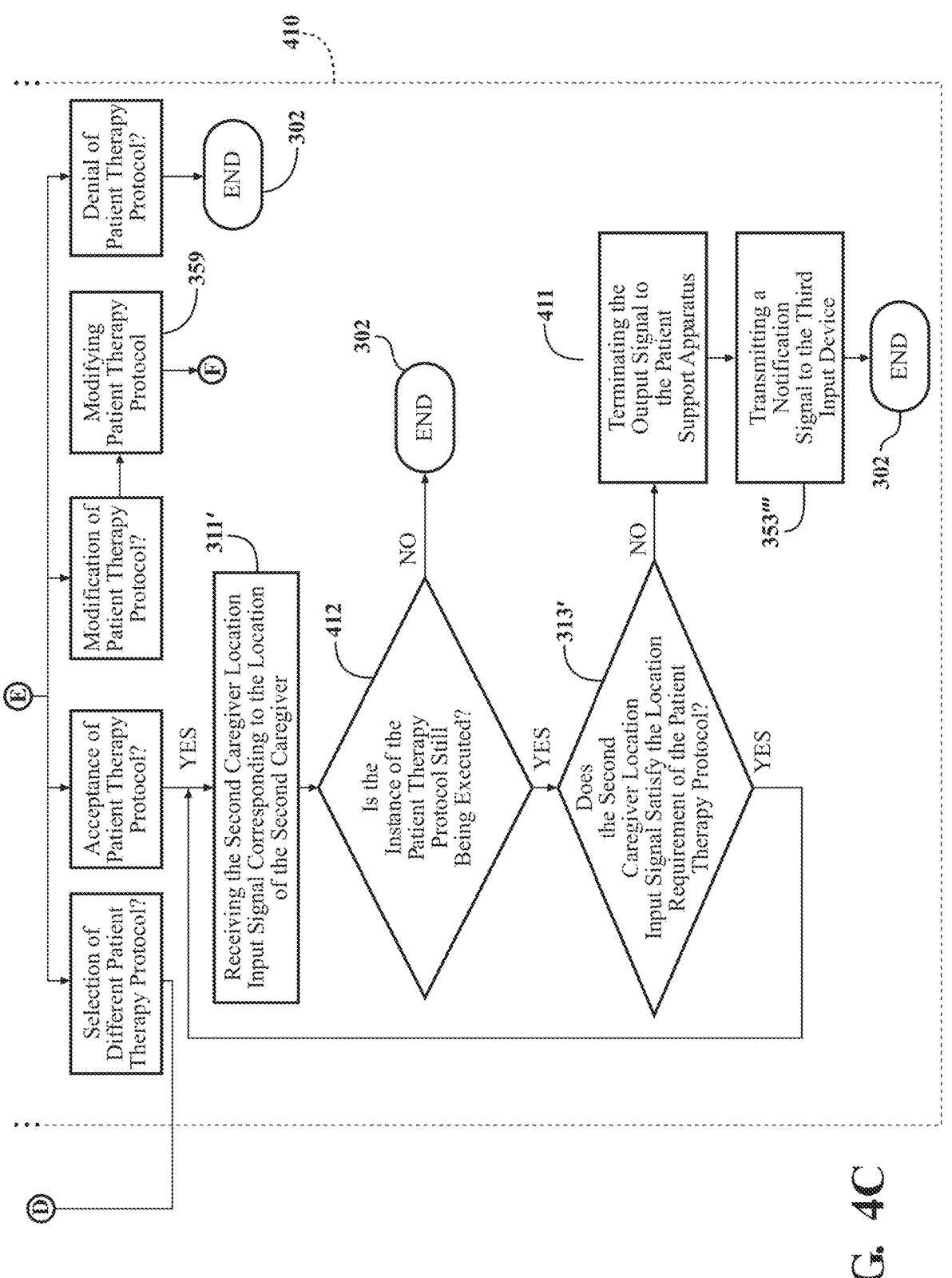
FIG. 4C is a flowchart further illustrating the step of monitoring the location of the caregiver.

FIG. 4C provides a flowchart illustrating the step 410 if the method receives a response during step 354'. As shown if the response is the acceptance of the selected patient therapy protocol, the method repeats step 311', step 412, and step 313'. Here, however, if the second caregiver location does not satisfy the location requirement of the patient therapy protocol during step 412, the method proceeds to step 411 and ultimately to step 302, the end of the method.

If the second caregiver location does satisfy the location requirement of the patient therapy protocol, the method returns to step 311' to once again receive the second caregiver location input signal.

Furthermore, the method may proceed to step 411 if the method receives the denial of the instance of the patient therapy protocol during step 354' the method may proceed to step 411 and terminate the patient-moving output signal to the patient support apparatus 100 before proceeding to step 302, the end of the end of the method. If the method receives the modification of the instance of the patient therapy protocol during step 354', the method may modify the patient therapy protocol during step 359 before returning to step 315 in FIG. 4B. If the method receives the selection of a different patient therapy protocol, the method may return to step 314 in FIG. 3B.

Additionally, in some embodiments of FIG. 4B, the method may continue transmitting the patient-moving output signal for a period of time, such as five minutes, even if the method does not receive the response to notifying the second caregiver 196 during step 354'.

In the previously described methods, the methods may, at any time, receive the control signal from the override system 194. Similar to the response received during step 354 and step 354' of the previously described methods, the control signal may be the acceptance of the patient therapy protocol, the denial of the patient therapy protocol, the modification to the patient therapy protocol, the selection of a different patient therapy protocol, or combinations thereof. As such, the method may proceed after receiving the control signal in the same way the method would proceed after receiving the response during step 354. For example, if the control signal is the denial of the patient therapy protocol, the method may proceed to step 302, or the end of the method. For reference, the method would proceed in the same way in response to receiving the denial of the patient therapy protocol during step 354.

It is to be understood that the method may be adapted for embodiments with a greater number of input devices and/or caregivers. For example, the method, after determining that the second caregiver location input signal does not satisfy the location requirement of the selected patient therapy protocol during step 313', may repeat steps 353', 311', 313', 358, 353", and 354' to determine whether any other input devices and/or any other caregivers satisfy the location requirement of the selected patient therapy protocol. In other words, if the method determines that the first caregiver 195 and second caregiver 196 do not satisfy the location requirement of the selected patient therapy protocol, the method may determine whether any other caregiver satisfies the location requirement.

It is to be appreciated that the steps shown in the above described methods may be ordered in any suitable fashion. For example, referring back to FIG. 3B, the method may determine whether the permission level of the second caregiver 196 satisfies the permission requirement of the patient therapy protocol during step 358 before determining whether or not the second caregiver 196 satisfies the location requirement of the patient therapy protocol during step 313. In another example from FIG. 3B, the method may receive the second caregiver location input signal during step 311' before notifying the first caregiver 195 and/or second caregiver 196 that the first caregiver location input signal does not satisfy the location requirement of the selected patient therapy protocol during step 353'.

It should be understood that, while embodiments discussed herein describe techniques for managing patient therapy protocols of patient support apparatuses 100, the techniques for managing patient therapy protocols may be applied to other medical devices. For instance, these medical devices may include equipment such as lights, televisions, temperature management systems, respirators, IV lines, heart rate monitors, surgical tools, or any other devices that may be used in medical procedures or in the provision of medical services to patients. Therefore, the techniques for managing patient therapy protocols may apply to any of the above-described medical devices, or any other medical device that may be used in medical procedures or in the provision of medical services to patients.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A system for managing treatment protocols across a communication network, the system comprising:
   a patient support apparatus coupled to the communication network for supporting a patient;
   an input device coupled to the communication network for use by a caregiver;
   an actuatable device coupled to the communication network for providing treatment to the patient;
   a location system configured to determine a location of the caregiver;
   an override system coupled to the communication network and configured to transmit a control signal; and
   a management system coupled to the communication network, wherein the management system is configured to:
      receive a caregiver location input signal from the location system corresponding to the location of the caregiver,
      receive a selection of a treatment protocol for the patient from the input device, wherein the selected treatment protocol comprises a location requirement,
      determine whether the caregiver location input signal satisfies the location requirement of the selected treatment protocol,
      transmit an output signal to the actuatable device to initiate the selected treatment protocol, and
      receive the control signal from the override system.

2. The system of claim 1, wherein the control signal comprises an acceptance of the treatment protocol, a denial of the treatment protocol, a modification to the treatment protocol, a selection of a different treatment protocol, or combinations thereof.

3. The system of claim 1, wherein the treatment protocol is further defined as a patient therapy protocol; and
   wherein the actuatable device is configured to at least partially move the patient to effect the patient therapy protocol.

4. The system of claim 3, wherein the output signal is further defined as a patient-moving output signal; and wherein the actuatable device is configured to at least partially move the patient to effect the patient therapy protocol.

5. The system of claim 3, wherein the actuatable device includes one or more actuators operatively attached to the patient support apparatus.

6. The system of claim 1, wherein the location requirement comprises a proximity to the patient support apparatus, a predetermined location, or combinations thereof.

7. The system of claim 1, wherein the selected treatment protocol comprises an instance of a command for moving the patient, and wherein the management system is configured to determine whether the caregiver location input signal satisfies the location requirement of the selected treatment protocol before executing the instance of a command for moving the patient.

8. The system of claim 1, wherein the selected treatment protocol comprises an instance of a command for moving the patient, and wherein the management system is configured to determine whether the caregiver location input signal satisfies the location requirement of the selected treatment protocol during execution of the instance of a command for moving the patient.

9. The system of claim 1, wherein the selected treatment protocol comprises an instance of a command for moving the patient, wherein the location requirement comprises a first location requirement and a subsequent location requirement, wherein the first location requirement is a location requirement for a first instance of the selected treatment protocol and the subsequent location requirement is a location requirement for a subsequent instance of the selected treatment protocol.

10. The system of claim 1, wherein the treatment protocol is selected from a first treatment protocol and a second treatment protocol, the first treatment protocol and the second treatment protocol having different location requirements.

11. The system of claim 1, wherein the location system comprises at least one of a software component and a hardware component of a computing device; and wherein the computing device is the input device and the location system is further configured to determine the location of the caregiver based on a location of the input device.

12. The system of claim 1, wherein the location system determines the location of the caregiver based on the location of the input device using an asset tracking system.

13. The system of claim 1, wherein the location requirement is based on medical procedure data, patient character-istic data, caregiver observation data, a patient condition of the patient, a state of the patient support apparatus, a risk level of the selected treatment protocol, patient preferences, medication data, prior injury data, or combinations thereof.

14. The system of claim 1, further comprising a second input device coupled to the communication network for use by a second caregiver.

15. The system of claim 14, wherein one or more of the input device and the second input device are mobile input devices and/or are disposed on the patient support apparatus.

16. The system of claim 14, wherein the location system is further configured to determine a location of the second caregiver; and wherein the management system is further configured to receive a second location input signal corresponding to the location of the second caregiver and to determine whether the second location input signal satisfies the location requirement of the selected treatment protocol.

17. The system of claim 16, further comprising a third input device coupled to the communication network for use by a third caregiver, wherein the management system is further configured to transmit a notification signal to the third input device based on the second location input signal and the location requirement of the selected treatment protocol.

18. The system of claim 16, wherein the management system is further configured to terminate the output signal to the actuatable device based on the second location input signal and the location requirements of the selected treatment protocol.

19. The system of claim 14, wherein the selected treatment protocol comprises a permission requirement, and wherein the management system is further configured to:

determine whether a permission level of the second caregiver satisfies the permission requirement of the selected treatment protocol; and transmit a notification signal to the second input device based on the permission level of the second caregiver and the permission requirement of the selected treatment protocol.

20. The system of claim 14, wherein the management system is further configured to transmit a notification signal to at least one of the input device and the second input device upon a determination that the caregiver location input signal does not satisfy the location requirement of the selected treatment protocol.

* * * * *